United States Patent

Nagao et al.

[11] 4,013,367
[45] Mar. 22, 1977

[54] APPARATUS FOR DETECTING IRREGULARITIES IN THE SURFACES OF MATERIALS

[75] Inventors: Yukio Nagao, Yamato; Masayoshi Shimada, Yokohama, both of Japan

[73] Assignee: Tokyo Shibaura Electric Co., Ltd., Japan

[22] Filed: May 13, 1975

[21] Appl. No.: 577,032

[30] Foreign Application Priority Data

May 13, 1974 Japan .............. 49-52271

[52] U.S. Cl. .............................. 356/200; 250/572; 350/7
[51] Int. Cl.² ...................................... G01N 21/32
[58] Field of Search ............. 250/571, 572; 350/6, 350/7; 356/199, 200, 159, 160, 167

[56] References Cited

UNITED STATES PATENTS

| | | | |
|---|---|---|---|
| 2,272,097 | 2/1942 | Smith | 250/572 |
| 3,060,319 | 10/1962 | Greunke | 250/571 |
| 3,307,968 | 3/1967 | Schnedler | 250/571 |
| 3,410,643 | 11/1968 | Jörgensen | 356/200 |
| 3,509,349 | 4/1970 | Molines et al. | 356/200 |
| 3,618,063 | 11/1971 | Johnson | 356/200 |
| 3,893,079 | 7/1975 | Shepard et al. | 350/6 |

*Primary Examiner*—Edward S. Bauer
*Assistant Examiner*—Richard A. Rosenberger
*Attorney, Agent, or Firm*—Oblon, Fisher, Spivak, McClelland & Maier

[57] ABSTRACT

An apparatus for detecting surface irregularities in a moving web is disclosed. The apparatus includes a laser light source, the output beam of which is divided into a plurality of zone scanning beams by an optical network. The plural beams are reflected by a rotating scanner to a series of reflecting surfaces, each oriented at a different angle to stagger the scanning beams. The staggered beams are again reflected from two groups of reflecting surfaces inclined in opposite directions relative to one another for separating the scanning zones covered by the scanning beams.

8 Claims, 3 Drawing Figures

APPARATUS FOR DETECTING IRREGULARITIES IN THE SURFACES OF MATERIALS

BACKGROUND OF THE INVENTION

1. Field of the Invention

This invention relates to an improvement in apparatus for detecting irregularities in the surfaces of materials.

2. Description of the Prior Art

Apparatuses for detecting irregularities in the surfaces of materials have been used extensively for detecting irregularities such as cracks, defects and the like in surfaces of materials such as steel or aluminum web, and the like, by means of detecting the light reflected by the surfaces of these materials. Apparatuses of this kind, wherein a laser is usually utilized as the source of light, detect with high speed, cracks, damage and the like in the surfaces of a planar steel member rolled by a rolling machine, for example.

Usually, in apparatuses adapted to be used with wide webs, the width of the surface to be scanned is divided into zones and a separate laser source is used for each zone. The beam of each laser is scanned widthwise in each zone so that the scan lines are in alignment with each other.

Apparatuses using multiple beams can, of course, inspect the surfaces of materials at higher speeds than apparatuses utilizing only a single beam. Hence, in such multi-beam apparatus no increase of the scanning speed or enlargement of the laser beam cross section is necessary for increasing the operating speed.

However, prior apparatuses using multiple laser beams have a drawback in that the detectors responsive to the reflected beams receive not only the individual reflected beam which is sought to be detected, but also reflected beams from adjacent scanning zones due to adjacent and aligned positions of the scanning zones. Hence the detection accuracy of such devices is not always very good.

SUMMARY OF THE INVENTION

Accordingly, it is an object of this invention to provide an improved apparatus for detecting irregularities in the surfaces of materials which is capable of detecting the irregularities in the surfaces of materials with improved accuracy.

Another object of this invention is to provide an improved multiple beam apparatus of the type described which can be constructed using only a single light source.

Briefly, these and other objects of the invention are accomplished by providing an apparatus for detecting irregularities in the surfaces of materials of the type described wherein a laser beam produced by a single laser source is divided into several beams by a dividing device including a half silvered mirror. The divided laser beams are reflected by first, second and third mirrors, and the beam reflected from the third mirror irradiates the surface of the material to be inspected such that laser spots on the surface are scanned widthwise in their respective zones.

BRIEF DESCRIPTION OF THE DRAWINGS

Further objects and advantages of the invention together with the organization thereof can be more fully understood from the following detailed description taken in conjunction with the accompanying drawings in which.

DESCRIPTION OF THE PREFERRED EMBODIMENTS

Figure 1:
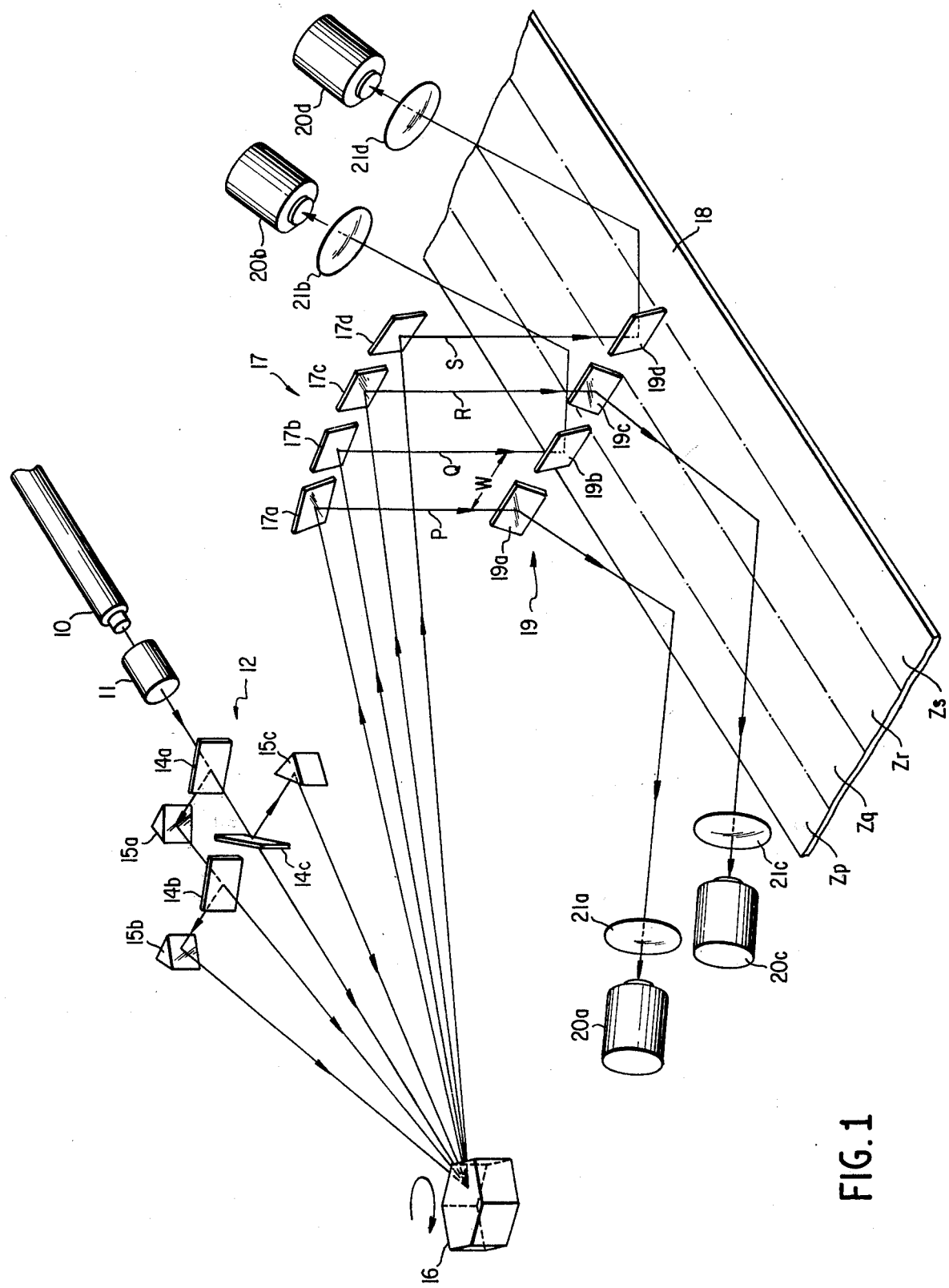
FIG. 1 is a perspective schematic illustration of one embodiment of the present invention.

Referring now to the drawings wherein like reference numerals designate identical or corresponding parts throughout the several views, and more particularly to FIG. 1 thereof a preferred embodiment of the invention is illustrated in which the surface to be detected is divided into four zones, for example. The light beam produced by a source of light such as a laser 10 is focused and converted to a fine, narrow beam of parallel light rays by condenser lens 11. A dividing device 12 having, for example, half silvered mirrors and prism deflectors is provided to divide the narrow parallel laser rays from the condenser lens 11 into several beams.

The laser beam from the condenser lens 11 is reflected from and transmitted through a half silvered mirror 14a and is divided into two laser beams. The direction of the reflected laser beam is changed by a deflector prism 15a, and then the beam is further reflected from and transmitted through a half silvered mirror 14b and is thus divided into two additional beams. The laser beam reflected from the mirror 14b is changed in its direction by a means such as a prism 15b. Thus one beam impinges on a first facet of a rotating mirror device 16, described hereinafter, and the other impinges on a prism 15b.

The beam transmitted through the half-silvered mirror 14a impinges on a half-silvered mirror 14c and is divided thereby into two beams. The beam transmitted through the mirror 14c impinges on the first mirror 16 and the beam reflected by the mirror 14c impinges on the prism 15c then impinges on the rotating mirror device 16.

The half silvered mirrors 14a, 14b, 14c and the deflectors 15a, 15b, 15c are oriented so that the divided laser beams fall upon one point-like portion on the surface of a first facet of the rotating mirror device 16 as shown in FIG. 1. As the first mirror device 16, a single mirror which is caused to be oscillated by a simple harmonic oscillator, or the like, may also be employed.

Figure 2:
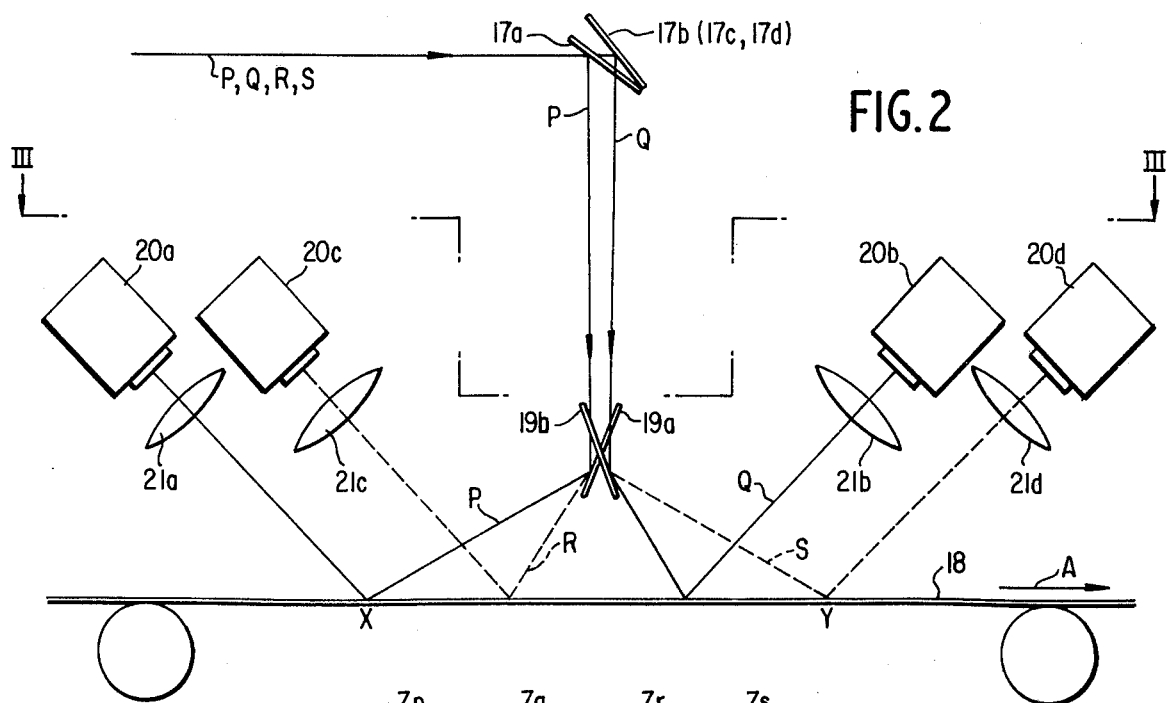
FIG. 2 is a side view of a portion of the apparatus of FIG. 1.
Figure 3:
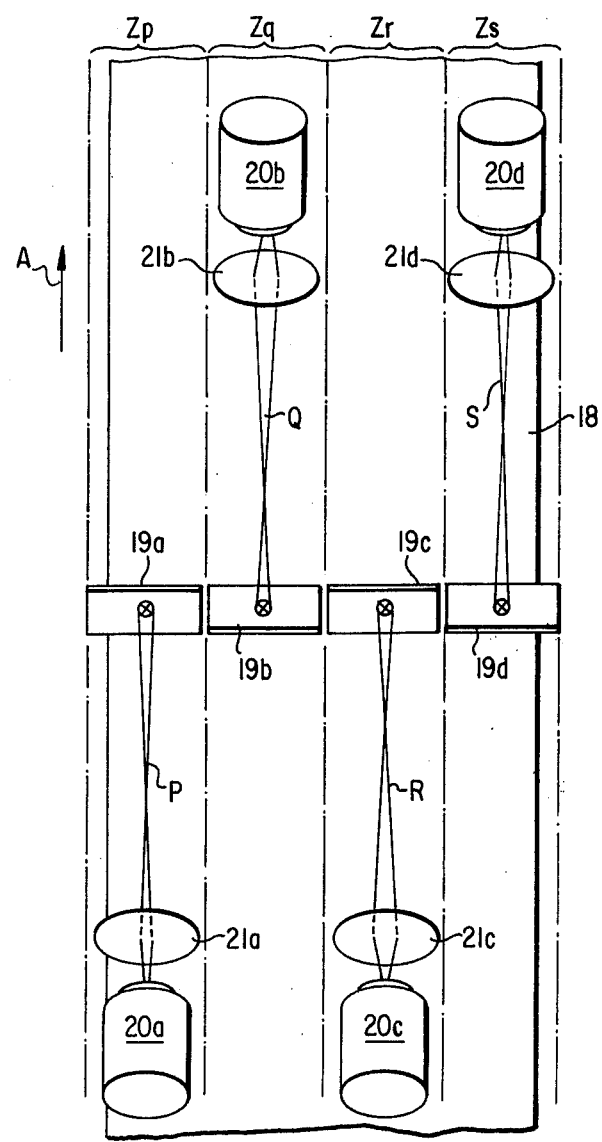
FIG. 3 is a plan view taken along the line III—III in FIG 2.

The laser beams supplied from deflector 15b, half silvered mirrors 14b, 14c, and deflector 15c are reflected by the first facet of the mirror device 16 and are respectively supplied to mirrors 17d, 17c, 17b and 17a of a second mirror device 17. The beams P, Q, R and S reflected from mirrors 17a, 17b, 17c and 17d impinge on the surface of a web material 18 through a third mirror device 19. The web material 18 runs, in FIG. 1, in a direction at an angle to the plane of the figure. In FIGS. 2 and 3 the web material 18 runs in a direction as shown by an arrow A.

The third mirror device 19 includes four mirrors 19a, 19b, 19c and 19d. As shown in FIG. 2, the mirrors 19a and 19c are disposed in one inclined plane, and the mirrors 19b and 19d are disposed in another inclined plane, these two planes being symmetrically inclined in opposite directions with respect to the vertical plane in which the beams P, Q, R and S are scanned. These mirrors cause the scanning zones to be separated and spaced from one another.

The laser beams P and R from the mirrors 17a and 17c are reflected by the mirrors 19a and 19c and then impinge on the surface of the web material at a position on the material 18 as shown at X. The beams Q and S similarly impinge on the surface at the position Y. In FIG. 1, the mirror device 16 rotates, causing a spot scanning action which, in turn, causes the beams P, Q, R and S impinging on the surface of the material 18, to scan across the surface.

The mirrors 17a, 17b, 17c and 17d are arranged at different angles such that the beams P, Q, R and S impinging on the material 18 scanning the virtual surface zones Zp, Zq, Zr and Zs, respectively, are out of phase with one another. Preferably, the width of the zones Zp, Zq, Zr and Zs have substantially the same value W. The total width of zones Zp, Zq, Zr and Zs is greater than the width of the material 18.

The beams reflected from the surface zones Zp, Zq, Zr and Zs are detected by light responsive devices 20a, 20b, 20c and 20d through condenser lenses 21a, 21b, 21c and 21d, respectively. The signals from the light responsive devices, or detectors, 20a, 20b, 20c and 20d are indicative of the surface condition of the material 18, thus the irregularities in the surface can be detected.

According to this embodiment, in which the surface of the material is divided into four zones, for example, each zone Zp, Zq, Zr and Zs is scanned by an identical laser beam. In addition, the scan lines in adjacent zones on the surface being studied are not aligned, but are staggered or out of phase relative to one another, whereby the reflected beam detectors are prevented from receiving the beams reflected from adjacent zones. Further, the apparatus of the invention is of simple construction due to the fact that a device for dividing a single laser beam into any required number of beams is used.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. An apparatus, for detecting irregularities in the surface of a material which is in relative motion with respect to said apparatus and which has a plurality of adjacent, virtual zones defined thereon, comprising:

means including a light source for producing a light beam, dividing means for dividing said light beam from said light source into several fine light beams and for conducting said divided beams to a scanning means;

scanning means for receiving said light beams from said dividing means and for scanning said light beams substantially perpendicularly to the direction of motion of said material across scanning zones of predetermined width defined on said surface of said material by said scanning means, the scanning zones defined upon adjacent virtual zones being respectively spaced apart from one another; and detecting means for receiving said light beams from said scanning means subsequent to its reflection from said surface of said material, said detecting means providing an indication of said surface irregularities.

2. The apparatus of claim 1 wherein:
said light source is a laser.

3. The apparatus of claim 1 wherein:
said dividing means comprises a condenser lens, half silvered mirrors and deflectors.

4. The apparatus of claim 1, wherein:
said scanning means comprises a first mirror device which receives said fine light beams from said dividing means,
a second mirror device which receives the light beams reflected by said first mirror device; and,
a third mirror device which receives the light beams from said second mirror device and reflects them onto said surface of said material to be studied.

5. The apparatus of claim 4 wherein:
said first mirror device is a rotating reflecting mirror.

6. The apparatus of claim 4 wherein:
said second mirror device is comprised of a plurality of individual mirrors, each disposed in a different inclined plane with respect to the others so that the light beams from said first mirror device impinge on said surface of said material in a staggered pattern.

7. The apparatus of claim 6 wherein:
said third mirror device comprises two groups of reflecting surfaces which are inclined in opposite directions with respect to one another.

8. The apparatus of claim 1 wherein:
said detecting means comprises several light responsive devices for receiving the respective light beams reflected by said material.

* * * * *